(12) United States Patent
Sepulveda et al.

(10) Patent No.: US 9,451,975 B2
(45) Date of Patent: Sep. 27, 2016

(54) SKIN ABRADER

(71) Applicant: iRhythmTechnologies, Inc., San Francisco, CA (US)

(72) Inventors: Genaro Sebastian Sepulveda, San Francisco, CA (US); Timothy Jon Bahney, San Francisco, CA (US); Shena Hae Park, San Francisco, CA (US)

(73) Assignee: iRhythm Technologies, Inc., San Francisco, CA (US)

( * ) Notice: Subject to any disclaimer, the term of this patent is extended or adjusted under 35 U.S.C. 154(b) by 0 days.

(21) Appl. No.: 14/831,078

(22) Filed: Aug. 20, 2015

(65) Prior Publication Data

US 2015/0351799 A1 Dec. 10, 2015

Related U.S. Application Data

(62) Division of application No. 14/247,014, filed on Apr. 7, 2014, now Pat. No. 9,173,670.

(60) Provisional application No. 61/809,817, filed on Apr. 8, 2013.

(51) Int. Cl.
*A61B 17/50* (2006.01)
*A61B 17/32* (2006.01)
(Continued)

(52) U.S. Cl.
CPC ............ *A61B 17/32* (2013.01); *A61B 5/04025* (2013.01); *A61B 5/04087* (2013.01); *A61B 17/54* (2013.01); *A61B 2017/320004* (2013.01); *A61B 2050/314* (2016.02)

(58) Field of Classification Search
CPC A61B 17/32; A61B 19/026; A61B 5/04025; A61B 5/04087; A61B 17/54; A61B 2019/0267; A61B 2017/320004; A61B 2017/00761; A47K 7/02; A61E 13/00; A61A 13/00
USPC ........ 600/372, 382, 386, 391, 392; 607/149, 607/152–153; 606/131–133; 132/75.6, 76.4
See application file for complete search history.

(56) References Cited

U.S. PATENT DOCUMENTS 1,497,079 A * 6/1924 Gullborg ................ A47K 7/028
　　　　　　　　　　　　　　　　　　　　　　15/143.1
2,179,922 A * 11/1939 Dana ...................... A45D 29/17
　　　　　　　　　　　　　　　　　　　　　　132/76.4
(Continued)

FOREIGN PATENT DOCUMENTS

CA　　　　2752154 A1　　8/2010
EP　　　　01782729 A1　　5/2007
(Continued)

OTHER PUBLICATIONS

U.S. Appl. No. 8,750,980, filed Jun. 10, 2014, Katra et al. (withdrawn).

(Continued)

*Primary Examiner* — Amy R Weisberg
(74) *Attorney, Agent, or Firm* — Knobbe, Martens, Olson & Bear LLP

(57) ABSTRACT

The present invention relates to devices, methods, and systems for abrading the skin in preparation for attachment of an electrode. In some embodiments, the invention may provide for a simple, low-cost device 120 with a flat, abrading surface that removes the topmost layer of the skin without causing undue injury.

22 Claims, 12 Drawing Sheets

(51) Int. Cl.
*A61B 5/0402* (2006.01)
*A61B 5/0408* (2006.01)
*A61B 17/54* (2006.01)

(56) References Cited

U.S. PATENT DOCUMENTS

| | | | |
|---|---|---|---|
| 2,201,645 A * | 5/1940 | Epner | B24D 15/023 15/231 |
| 2,311,060 A * | 2/1943 | Lurrain | A45D 26/0004 451/524 |
| 2,500,840 A * | 3/1950 | Lyons | A47L 13/29 15/111 |
| 3,215,136 A | 11/1965 | Holter et al. | |
| 3,547,107 A | 12/1970 | Chapman et al. | |
| 3,870,034 A | 3/1975 | James | |
| 3,882,853 A * | 5/1975 | Gofman | A61B 5/0416 600/391 |
| 3,911,906 A * | 10/1975 | Reinhold, Jr. | A61B 5/04025 600/392 |
| 4,023,312 A * | 5/1977 | Stickney | A47J 37/06 451/357 |
| 4,027,664 A * | 6/1977 | Heavner, Jr. | A61B 5/411 600/376 |
| 4,121,573 A | 10/1978 | Crovella et al. | |
| 4,123,785 A | 10/1978 | Cherry et al. | |
| 4,126,126 A * | 11/1978 | Bare | A61B 5/0408 439/909 |
| 4,202,139 A * | 5/1980 | Hong | B24D 15/045 15/227 |
| 4,274,419 A | 6/1981 | Tam et al. | |
| 4,274,420 A * | 6/1981 | Hymes | A61B 5/04087 600/391 |
| 4,286,610 A * | 9/1981 | Jones | A45D 29/12 132/76.4 |
| 4,333,475 A | 6/1982 | Moreno et al. | |
| 4,361,990 A * | 12/1982 | Link | B24D 15/023 451/524 |
| 4,381,792 A * | 5/1983 | Busch, Jr. | A45D 29/12 132/75.6 |
| 4,438,767 A * | 3/1984 | Nelson | A61B 19/00 30/169 |
| 4,459,987 A * | 7/1984 | Pangburn | B24D 15/04 132/76.4 |
| 4,535,783 A | 8/1985 | Marangoni | |
| 4,537,207 A * | 8/1985 | Gilhaus | A61B 17/54 132/76.4 |
| 4,572,187 A | 2/1986 | Schetrumpf | |
| 4,621,465 A * | 11/1986 | Pangburn | B24D 15/023 132/76.4 |
| 4,658,826 A * | 4/1987 | Weaver | A61B 5/0408 252/519.21 |
| 4,712,552 A * | 12/1987 | Pangburn | B24D 15/04 132/76.4 |
| 4,736,752 A | 4/1988 | Munck et al. | |
| 4,925,453 A * | 5/1990 | Kannankeril | A61F 13/36 128/917 |
| 4,981,141 A | 1/1991 | Segalowitz | |
| 5,003,987 A * | 4/1991 | Grinwald | A61B 5/0531 600/306 |
| 5,027,824 A | 7/1991 | Dougherty et al. | |
| 5,086,778 A | 2/1992 | Mueller et al. | |
| 5,205,295 A | 4/1993 | Del Mar et al. | |
| 5,228,450 A | 7/1993 | Sellers | |
| 5,230,119 A * | 7/1993 | Woods | A45D 40/26 128/917 |
| 5,289,824 A | 3/1994 | Mills et al. | |
| 5,305,746 A * | 4/1994 | Fendrock | A61B 5/0408 600/391 |
| 5,309,909 A * | 5/1994 | Gadsby | A61B 5/0408 600/386 |
| 5,365,935 A | 11/1994 | Righter et al. | |
| 5,458,141 A * | 10/1995 | Neil | A61B 5/0408 600/386 |
| 5,483,967 A | 1/1996 | Ohtake | |
| 5,489,624 A | 2/1996 | Kantner et al. | |
| 5,511,553 A | 4/1996 | Segalowitz | |
| 5,515,858 A | 5/1996 | Myllymaki | |
| 5,536,768 A | 7/1996 | Kantner et al. | |
| 5,626,140 A | 5/1997 | Feldman et al. | |
| 5,634,468 A | 6/1997 | Platt et al. | |
| 5,645,063 A * | 7/1997 | Straka, Jr. | A61B 5/04085 600/391 |
| 5,645,068 A | 7/1997 | Mezack et al. | |
| 5,730,143 A | 3/1998 | Schwarzberg | |
| 5,749,365 A | 5/1998 | Magill | |
| 5,749,367 A | 5/1998 | Gamlyn et al. | |
| 5,771,524 A * | 6/1998 | Woods | A45D 40/00 15/209.1 |
| 5,881,743 A * | 3/1999 | Nadel | A45D 34/06 132/317 |
| 5,957,854 A | 9/1999 | Besson et al. | |
| 5,959,529 A | 9/1999 | Kail | |
| 6,013,007 A | 1/2000 | Root et al. | |
| 6,032,060 A * | 2/2000 | Carim | A61N 1/0472 128/898 |
| 6,044,515 A * | 4/2000 | Zygmont | B05C 17/00 15/209.1 |
| 6,093,146 A | 7/2000 | Filangeri | |
| D429,336 S | 8/2000 | Francis et al. | |
| 6,102,856 A | 8/2000 | Groff et al. | |
| 6,117,077 A | 9/2000 | Del Mar et al. | |
| 6,134,480 A | 10/2000 | Minogue | |
| 6,136,008 A * | 10/2000 | Becker | A61B 5/04025 600/392 |
| 6,161,036 A * | 12/2000 | Matsumura | A61B 5/0006 128/903 |
| 6,169,915 B1 | 1/2001 | Krumbiegel et al. | |
| 6,178,357 B1 | 1/2001 | Gliner et al. | |
| 6,200,265 B1 | 3/2001 | Walsh et al. | |
| 6,225,901 B1 | 5/2001 | Kail | |
| 6,232,366 B1 | 5/2001 | Wang et al. | |
| 6,238,338 B1 | 5/2001 | DeLuca et al. | |
| 6,248,115 B1 * | 6/2001 | Halk | A45D 26/0004 132/76.4 |
| 6,290,707 B1 * | 9/2001 | Street | A61B 17/54 606/131 |
| 6,379,237 B1 * | 4/2002 | Gordon | E04F 21/00 451/523 |
| 6,385,473 B1 | 5/2002 | Haines et al. | |
| 6,416,471 B1 | 7/2002 | Kumar et al. | |
| 6,434,410 B1 | 8/2002 | Cordero et al. | |
| 6,454,708 B1 | 9/2002 | Ferguson et al. | |
| 6,456,872 B1 | 9/2002 | Faisandier | |
| 6,464,815 B1 * | 10/2002 | Beaudry | A45D 29/11 15/208 |
| 6,493,898 B1 * | 12/2002 | Woods | B05C 17/00 15/209.1 |
| 6,510,339 B2 | 1/2003 | Kovtun et al. | |
| 6,546,285 B1 | 4/2003 | Owen et al. | |
| 6,569,095 B2 | 5/2003 | Eggers | |
| 6,580,942 B1 | 6/2003 | Willshire | |
| 6,585,707 B2 | 7/2003 | Cabiri et al. | |
| 6,589,187 B1 | 7/2003 | Dirnberger et al. | |
| 6,605,046 B1 | 8/2003 | Del Mar | |
| 6,622,035 B1 * | 9/2003 | Merilainen | A61B 5/04025 600/391 |
| 6,626,865 B1 * | 9/2003 | Prisell | A61B 17/32053 604/116 |
| 6,664,893 B1 | 12/2003 | Eveland et al. | |
| 6,665,385 B2 | 12/2003 | Rogers et al. | |
| 6,690,959 B2 * | 2/2004 | Thompson | A61B 5/0006 600/372 |
| 6,694,177 B2 | 2/2004 | Eggers et al. | |
| 6,701,184 B2 | 3/2004 | Henkin | |
| 6,711,427 B1 * | 3/2004 | Ketelhohn | A61B 5/04025 600/372 |
| 6,730,028 B2 * | 5/2004 | Eppstein | A61B 10/0045 102/201 |
| 6,775,566 B2 | 8/2004 | Nissila | |
| 6,801,137 B2 | 10/2004 | Eggers | |
| 6,801,802 B2 | 10/2004 | Sitzman et al. | |
| 6,881,191 B2 | 4/2005 | Oakley et al. | |
| 6,893,396 B2 | 5/2005 | Schulze et al. | |
| 6,940,403 B2 | 9/2005 | Kail | |

(56) References Cited

U.S. PATENT DOCUMENTS

| | | |
|---|---|---|
| 6,954,163 B2 | 10/2005 | Toumazou et al. |
| 6,957,107 B2 | 10/2005 | Rogers et al. |
| 7,002,468 B2 | 2/2006 | Eveland et al. |
| 7,020,508 B2 | 3/2006 | Stivoric et al. |
| 7,024,248 B2 | 4/2006 | Penner et al. |
| 7,072,708 B1 | 7/2006 | Andresen et al. |
| 7,072,709 B2 | 7/2006 | Xue |
| 7,076,283 B2 | 7/2006 | Cho et al. |
| 7,076,287 B2 | 7/2006 | Rowlandson |
| 7,076,288 B2 | 7/2006 | Skinner |
| 7,076,289 B2 | 7/2006 | Sarkar et al. |
| 7,079,977 B2 | 7/2006 | Osorio et al. |
| 7,082,327 B2 | 7/2006 | Houben |
| 7,099,715 B2 | 8/2006 | Korzinov et al. |
| 7,130,396 B2 | 10/2006 | Rogers et al. |
| 7,179,152 B1 * | 2/2007 | Rhoades ............... A61K 8/19 424/401 |
| 7,193,264 B2 | 3/2007 | Lande |
| 7,194,300 B2 | 3/2007 | Korzinov |
| 7,206,630 B1 | 4/2007 | Tarler |
| 7,212,850 B2 | 5/2007 | Prystowsky et al. |
| 7,242,318 B2 | 7/2007 | Harris |
| 7,266,361 B2 | 9/2007 | Burdett |
| 7,316,671 B2 * | 1/2008 | Lastovich ........... A61B 17/205 604/290 |
| 7,354,423 B2 * | 4/2008 | Zelickson ......... A45D 26/0004 604/289 |
| 7,387,607 B2 | 6/2008 | Holt et al. |
| 7,481,772 B2 | 1/2009 | Banet |
| 7,482,314 B2 * | 1/2009 | Grimes ............... A61B 17/50 424/401 |
| 7,502,643 B2 | 3/2009 | Farringdon et al. |
| 7,587,237 B2 | 9/2009 | Korzinov et al. |
| 7,630,756 B2 | 12/2009 | Linker |
| 7,632,174 B2 * | 12/2009 | Gringer ................ B24D 15/04 451/344 |
| 7,729,753 B2 | 6/2010 | Kremliovsky et al. |
| D621,048 S | 8/2010 | Severe et al. |
| 7,815,494 B2 | 10/2010 | Gringer et al. |
| 7,841,039 B1 * | 11/2010 | Squire .................... A47L 13/12 15/118 |
| 7,889,070 B2 | 2/2011 | Reeves et al. |
| D634,431 S | 3/2011 | Severe et al. |
| 7,907,956 B2 | 3/2011 | Uhlik |
| 7,907,996 B2 | 3/2011 | Prystowsky et al. |
| 7,941,207 B2 | 5/2011 | Korzinov |
| 7,996,075 B2 | 8/2011 | Korzinov et al. |
| 8,002,701 B2 | 8/2011 | Michael et al. |
| 8,077,042 B2 | 12/2011 | Peeters |
| 8,116,841 B2 | 2/2012 | Bly et al. |
| 8,150,502 B2 | 4/2012 | Kumar et al. |
| 8,156,945 B2 * | 4/2012 | Hart ..................... A61B 17/54 132/76.4 |
| 8,160,682 B2 | 4/2012 | Kumar et al. |
| D659,836 S | 5/2012 | Bensch et al. |
| 8,200,319 B2 | 6/2012 | Pu et al. |
| 8,214,007 B2 | 7/2012 | Baker et al. |
| 8,244,335 B2 | 8/2012 | Kumar et al. |
| 8,249,686 B2 | 8/2012 | Libbus et al. |
| 8,261,754 B2 * | 9/2012 | Pitstick ................. A45D 29/04 132/323 |
| RE43,767 E | 10/2012 | Eggers et al. |
| 8,285,356 B2 | 10/2012 | Bly et al. |
| 8,290,129 B2 | 10/2012 | Rogers et al. |
| 8,326,407 B2 | 12/2012 | Linker |
| 8,343,116 B2 * | 1/2013 | Ignon ................ A61M 35/003 604/289 |
| 8,374,688 B2 | 2/2013 | Libbus et al. |
| 8,406,843 B2 | 3/2013 | Tiegs et al. |
| 8,412,317 B2 | 4/2013 | Mazar |
| 8,425,414 B2 | 4/2013 | Eveland |
| 8,452,356 B2 | 5/2013 | Vestel et al. |
| 8,460,189 B2 | 6/2013 | Libbus et al. |
| 8,473,047 B2 | 6/2013 | Chakravarthy et al. |
| 8,515,529 B2 | 8/2013 | Pu et al. |
| 8,538,503 B2 | 9/2013 | Kumar et al. |
| 8,540,731 B2 * | 9/2013 | Kay .................... A61B 17/54 606/131 |
| 8,560,046 B2 | 10/2013 | Kumar et al. |
| 8,591,430 B2 | 11/2013 | Amurthur et al. |
| 8,594,763 B1 * | 11/2013 | Bibian ............... A61B 5/0478 600/372 |
| 8,684,925 B2 | 4/2014 | Amurthur et al. |
| 8,688,190 B2 | 4/2014 | Libbus et al. |
| 8,718,752 B2 | 5/2014 | Libbus et al. |
| 8,782,308 B2 | 7/2014 | Vlach |
| 8,790,257 B2 | 7/2014 | Libbus et al. |
| 8,795,174 B2 | 8/2014 | Manicka et al. |
| 8,818,481 B2 | 8/2014 | Bly et al. |
| 8,823,490 B2 | 9/2014 | Libbus et al. |
| 8,909,832 B2 | 12/2014 | Vlach et al. |
| 8,945,019 B2 | 2/2015 | Prystowsky et al. |
| 9,017,256 B2 | 4/2015 | Gottesman |
| 9,021,161 B2 | 4/2015 | Vlach et al. |
| 9,021,165 B2 | 4/2015 | Vlach |
| 9,173,670 B2 | 11/2015 | Sepulveda et al. |
| 9,179,851 B2 | 11/2015 | Baumann et al. |
| 9,241,649 B2 | 1/2016 | Kumar et al. |
| 2001/0056262 A1 | 12/2001 | Cabiri et al. |
| 2002/0067256 A1 | 6/2002 | Kail |
| 2002/0082491 A1 | 6/2002 | Nissila |
| 2002/0087167 A1 * | 7/2002 | Winitsky ............... A61B 17/32 606/131 |
| 2003/0069510 A1 | 4/2003 | Semler et al. |
| 2003/0083559 A1 | 5/2003 | Thompson |
| 2003/0149349 A1 | 8/2003 | Jensen |
| 2003/0176795 A1 | 9/2003 | Harris et al. |
| 2003/0195408 A1 * | 10/2003 | Hastings ............... A61B 5/411 600/382 |
| 2003/0199811 A1 * | 10/2003 | Sage, Jr. ............. A61B 17/205 604/46 |
| 2004/0032957 A1 | 2/2004 | Mansy et al. |
| 2004/0077954 A1 | 4/2004 | Oakley et al. |
| 2004/0215091 A1 | 10/2004 | Lohman et al. |
| 2004/0236202 A1 | 11/2004 | Burton |
| 2004/0254587 A1 * | 12/2004 | Park ..................... A61B 17/54 606/131 |
| 2004/0260189 A1 | 12/2004 | Eggers et al. |
| 2005/0096513 A1 | 5/2005 | Ozguz et al. |
| 2005/0101875 A1 | 5/2005 | Semler et al. |
| 2005/0118246 A1 | 6/2005 | Wong et al. |
| 2005/0119580 A1 | 6/2005 | Eveland |
| 2005/0165323 A1 | 7/2005 | Montgomery et al. |
| 2005/0277841 A1 | 12/2005 | Shennib |
| 2005/0280531 A1 | 12/2005 | Fadem et al. |
| 2006/0030781 A1 | 2/2006 | Shennib |
| 2006/0030782 A1 | 2/2006 | Shennib |
| 2006/0047215 A1 | 3/2006 | Newman et al. |
| 2006/0084883 A1 | 4/2006 | Linker |
| 2006/0142648 A1 | 6/2006 | Banet et al. |
| 2006/0142654 A1 | 6/2006 | Rytky |
| 2006/0149156 A1 | 7/2006 | Cochran et al. |
| 2006/0155173 A1 | 7/2006 | Anttila et al. |
| 2006/0155183 A1 | 7/2006 | Kroecker et al. |
| 2006/0155199 A1 | 7/2006 | Logier et al. |
| 2006/0155200 A1 | 7/2006 | Ng et al. |
| 2006/0161064 A1 | 7/2006 | Watrous et al. |
| 2006/0161065 A1 | 7/2006 | Elion |
| 2006/0161066 A1 | 7/2006 | Elion |
| 2006/0161067 A1 | 7/2006 | Elion |
| 2006/0161068 A1 | 7/2006 | Hastings et al. |
| 2006/0224072 A1 | 10/2006 | Shennib |
| 2006/0264767 A1 | 11/2006 | Shennib |
| 2007/0003695 A1 | 1/2007 | Tregub et al. |
| 2007/0010729 A1 * | 1/2007 | Virtanen ............ A61B 5/04025 600/391 |
| 2007/0088419 A1 | 4/2007 | Florina et al. |
| 2007/0156054 A1 | 7/2007 | Korzinov et al. |
| 2007/0225611 A1 | 9/2007 | Kumar et al. |
| 2007/0249946 A1 | 10/2007 | Kumar et al. |
| 2007/0255153 A1 | 11/2007 | Kumar et al. |
| 2007/0270678 A1 | 11/2007 | Fadem et al. |
| 2007/0293776 A1 | 12/2007 | Korzinov et al. |
| 2008/0039730 A1 | 2/2008 | Pu et al. |

(56) References Cited

U.S. PATENT DOCUMENTS

| | | |
|---|---|---|
| 2008/0091089 A1 | 4/2008 | Guillory et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0275327 A1 | 11/2008 | Faarbaek et al. |
| 2008/0288026 A1 | 11/2008 | Cross et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0182204 A1 | 7/2009 | Semler et al. |
| 2009/0253975 A1* | 10/2009 | Tiegs .................. A61B 5/0416 600/372 |
| 2009/0292194 A1 | 11/2009 | Libbus et al. |
| 2010/0022864 A1* | 1/2010 | Cordero .............. A61B 5/0478 600/372 |
| 2010/0042113 A1* | 2/2010 | Mah .................... C11D 11/0011 606/131 |
| 2010/0051039 A1* | 3/2010 | Ferrara .............. A45D 26/0004 128/898 |
| 2010/0056881 A1 | 3/2010 | Libbus et al. |
| 2010/0057056 A1* | 3/2010 | Gurtner .......... A61B 17/320016 604/542 |
| 2010/0081913 A1 | 4/2010 | Cross et al. |
| 2010/0145359 A1* | 6/2010 | Keller .................... A61B 17/54 606/131 |
| 2010/0191310 A1 | 7/2010 | Bly |
| 2010/0234716 A1 | 9/2010 | Engel |
| 2010/0249625 A1 | 9/2010 | Lin |
| 2010/0268103 A1 | 10/2010 | McNamara et al. |
| 2010/0331711 A1 | 12/2010 | Krauss et al. |
| 2011/0021937 A1 | 1/2011 | Hugh et al. |
| 2011/0087083 A1 | 4/2011 | Poeze et al. |
| 2011/0144470 A1 | 6/2011 | Mazar et al. |
| 2011/0160601 A1 | 6/2011 | Wang et al. |
| 2011/0166468 A1 | 7/2011 | Prystowsky et al. |
| 2011/0306862 A1* | 12/2011 | Hayes-Gill ........ A61B 5/04085 600/382 |
| 2012/0071730 A1 | 3/2012 | Romero |
| 2012/0071731 A1 | 3/2012 | Gottesman |
| 2012/0083670 A1 | 4/2012 | Rotondo et al. |
| 2012/0108917 A1 | 5/2012 | Libbus et al. |
| 2012/0108920 A1 | 5/2012 | Bly et al. |
| 2012/0110226 A1 | 5/2012 | Vlach et al. |
| 2012/0110228 A1 | 5/2012 | Vlach et al. |
| 2012/0172676 A1 | 7/2012 | Penders et al. |
| 2012/0197150 A1 | 8/2012 | Cao et al. |
| 2012/0271141 A1* | 10/2012 | Davies .................. A61B 5/053 600/382 |
| 2012/0310070 A1 | 12/2012 | Kumar et al. |
| 2012/0323257 A1* | 12/2012 | Sutton .................... A61B 17/54 606/131 |
| 2013/0046151 A1 | 2/2013 | Bsoul et al. |
| 2013/0085347 A1 | 4/2013 | Manicka et al. |
| 2013/0096395 A1 | 4/2013 | Katra et al. |
| 2013/0116533 A1 | 5/2013 | Lian et al. |
| 2013/0116585 A1 | 5/2013 | Bouguerra |
| 2013/0144146 A1 | 6/2013 | Linker |
| 2013/0225938 A1 | 8/2013 | Vlach |
| 2013/0226018 A1 | 8/2013 | Kumar et al. |
| 2013/0245415 A1 | 9/2013 | Kumar et al. |
| 2013/0245472 A1 | 9/2013 | Eveland |
| 2013/0253285 A1 | 9/2013 | Bly et al. |
| 2013/0274584 A1 | 10/2013 | Finlay et al. |
| 2013/0296680 A1 | 11/2013 | Linker |
| 2013/0300575 A1 | 11/2013 | Kurzweil et al. |
| 2013/0324868 A1 | 12/2013 | Kaib et al. |
| 2013/0331665 A1 | 12/2013 | Bly et al. |
| 2013/0338448 A1 | 12/2013 | Libbus et al. |
| 2014/0012154 A1 | 1/2014 | Mazar |
| 2014/0058280 A1 | 2/2014 | Chefles et al. |
| 2014/0094709 A1 | 4/2014 | Korzinov et al. |
| 2014/0206977 A1 | 7/2014 | Bahney et al. |
| 2015/0057512 A1 | 2/2015 | Kapoor |
| 2015/0081959 A1 | 3/2015 | Vlach et al. |
| 2015/0082623 A1 | 3/2015 | Felix et al. |
| 2015/0087921 A1 | 3/2015 | Felix et al. |
| 2015/0087922 A1 | 3/2015 | Bardy et al. |
| 2015/0087923 A1 | 3/2015 | Bardy et al. |
| 2015/0087948 A1 | 3/2015 | Bishay et al. |
| 2015/0087949 A1 | 3/2015 | Felix et al. |
| 2015/0087950 A1 | 3/2015 | Felix et al. |
| 2015/0087951 A1 | 3/2015 | Felix et al. |
| 2015/0088007 A1 | 3/2015 | Bardy et al. |
| 2015/0088020 A1 | 3/2015 | Dreisbach et al. |
| 2015/0173671 A1 | 6/2015 | Paalasmaa et al. |
| 2015/0297134 A1 | 10/2015 | Albert et al. |
| 2015/0327781 A1 | 11/2015 | Hernandez-Silverira et al. |

FOREIGN PATENT DOCUMENTS

| | | |
|---|---|---|
| EP | 2262419 A2 | 12/2010 |
| EP | 2395911 A2 | 12/2011 |
| EP | 2635179 A1 | 9/2013 |
| EP | 2635180 A1 | 9/2013 |
| GB | 2348707 A | 10/2000 |
| JP | 08-317913 A | 3/1996 |
| JP | 2000-126145 A | 5/2000 |
| JP | 2001-057967 A | 3/2001 |
| JP | 2004-121360 A | 4/2004 |
| JP | 2007-045967 A | 2/2007 |
| JP | 2007-296266 A | 11/2007 |
| JP | 2009-525816 A | 7/2009 |
| WO | WO 99/23943 A1 | 5/1999 |
| WO | WO 01/16607 A2 | 3/2001 |
| WO | WO 2005/037946 A1 | 4/2005 |
| WO | WO 2005/084533 A1 | 9/2005 |
| WO | WO 2006/094513 A2 | 9/2006 |
| WO | WO 2007/049080 A1 | 3/2007 |
| WO | WO 2007/036748 A2 | 4/2007 |
| WO | WO 2007/063436 A1 | 6/2007 |
| WO | WO 2007/072069 A2 | 6/2007 |
| WO | WO 2008/057884 A2 | 5/2008 |
| WO | WO 2010/093900 | 10/2010 |
| WO | WO 2011/077097 A1 | 6/2011 |
| WO | WO 2011/149755 A1 | 12/2011 |
| WO | WO 2012/009453 A2 | 1/2012 |
| WO | WO 2012/061509 | 5/2012 |
| WO | WO 2012/061518 | 5/2012 |
| WO | WO 2014/116825 | 7/2014 |

OTHER PUBLICATIONS

3M Corporation, "3M Surgical Tapes—Choose the Correct Tape" quicksheet (2004).

Del Mar et al.; The history of clinical holter monitoring; A.N.E.; vol. 10; No. 2; pp. 226-230; Apr. 2005.

Enseleit et al.; Long-term continuous external electrocardiographic recording: a review; Europace; vol. 8; pp. 255-266; 2006.

Hoefman et al.; Optimal duration of event recording for diagnosis of arrhythmias in patients with palpitations and light-headedness in the general practice; Family Practice; Dec. 7, 2006.

International Search Report issued on Sep. 23, 2014 for International Application No. PCT/US2013/033064.

Kennedy et al.; The history, science, and innovation of holter technology; A.N.E.; vol. 11; No. 1; pp. 85-84; 2006.

Mundt et al. "A Multiparameter Wearable Physiologic Monitoring System for Space and Terrestrial Applications" IEEE Transactions on Information Technology in Biomedicine, vol. 9, No. 3, pp. 382-384, Sep. 2005.

(56) References Cited

OTHER PUBLICATIONS

Reiffel et al., Comparison of autotriggered memory loop recorders versus standard loop recorders versus 24-hour holer monitors for arrhythmia detection; Am. J. Cardiology; vol. 95; pp. 1055-1059; May 1, 2005.
Request for Reexamination of U.S. Pat. No. 7,020,508 under 35 U.S.C. §§ 311-318 and 37 C.F.R. § 1.913 as submitted Sep. 14, 2012 in 78 pages.
Scapa Medical product listing and descriptions (2008) available at http://www.caapana.com/productlist.jsp and http://www.metplus.co.rs/pdf/prospekti/Samolepljivemedicinsketrake.pdf; retrieved via WayBack Machine Sep. 24, 2012.
Ward et al., Assessment of the diagnostic value of 24-hou ambulatory electrocardiographic monitoring; Biotelemetry Patient monitoring; vol. 7; 1980.
Ziegler et al; Comparison of continuous versus intermittent monitoring of atrial arrhythmias; Heart Rhythm; vol. 3; No. 12; pp. 1445-1452; Dec. 2006.
Zimetbaum et al., The evolving role of ambulatory arrhythmia monitoring in general clinic practice; Ann. Intern. Med.; vol. 130; pp. 848-8556; 1999.
Zimetbaum et al.; Utility of patient-activated cardiac event recorders in general clinical practice; The Amer. J. of Cardiology; vol. 79; Feb. 1, 1997.
U.S. Appl. No. 15/005,854, filed Jan. 25, 2016, Kumar et al.

\* cited by examiner

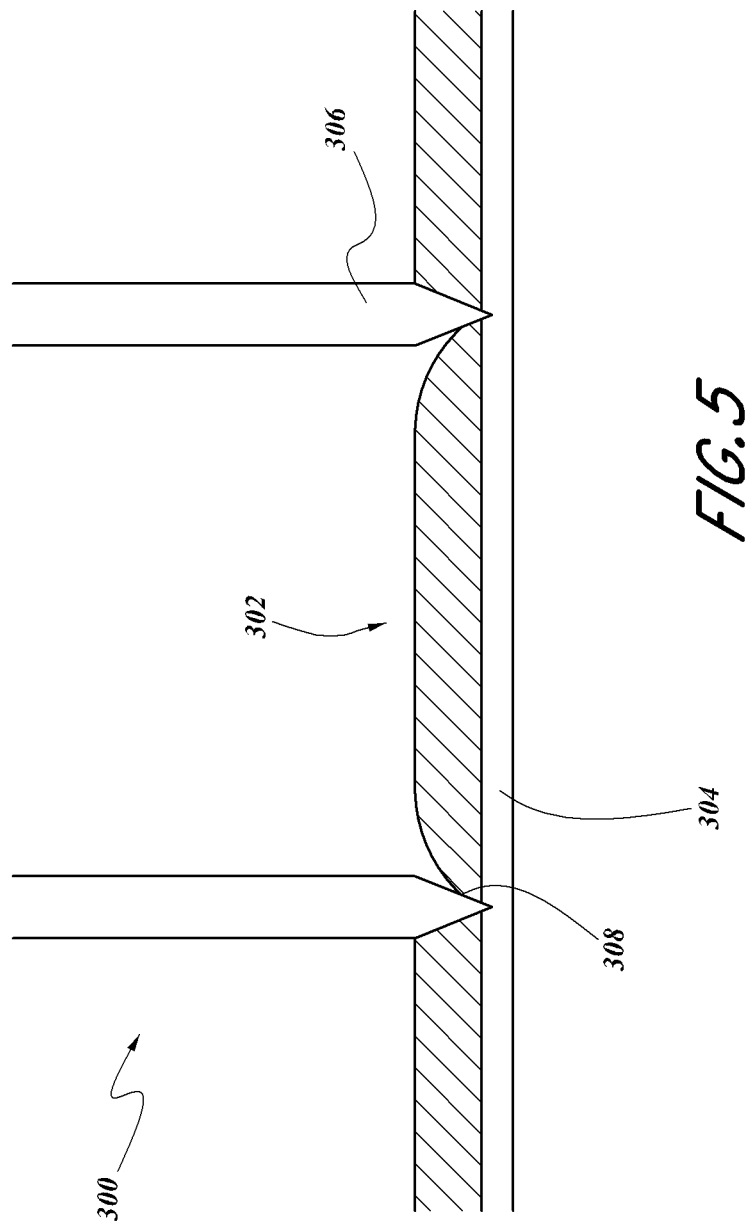

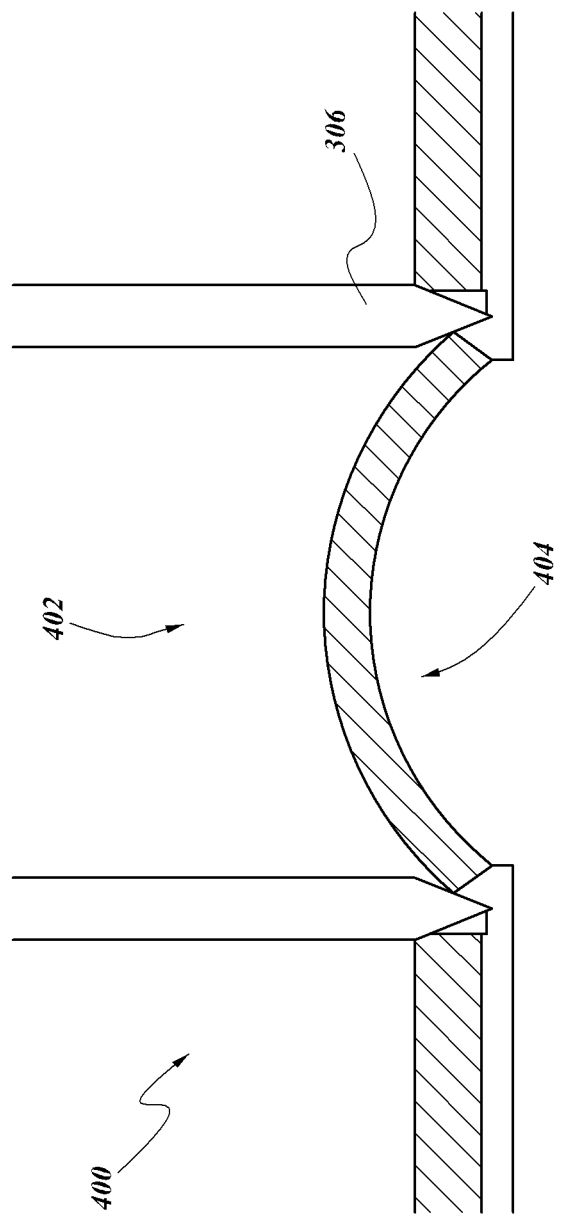

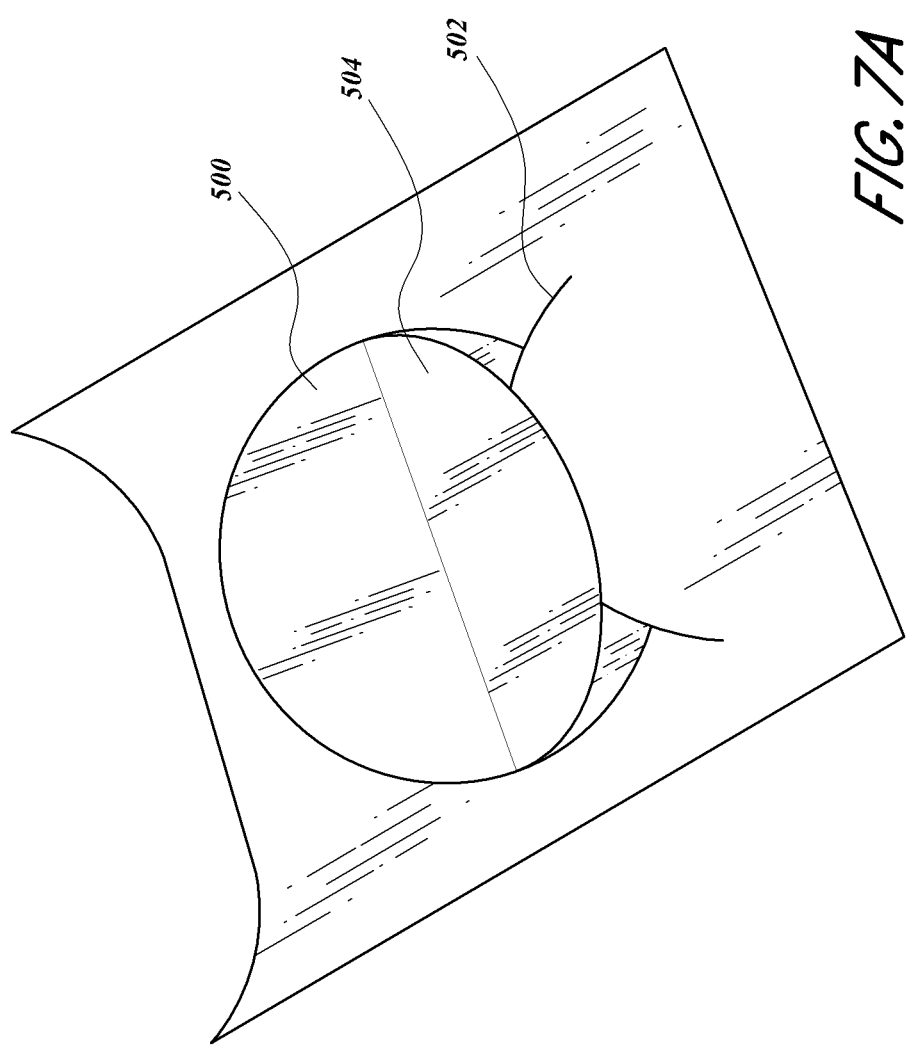

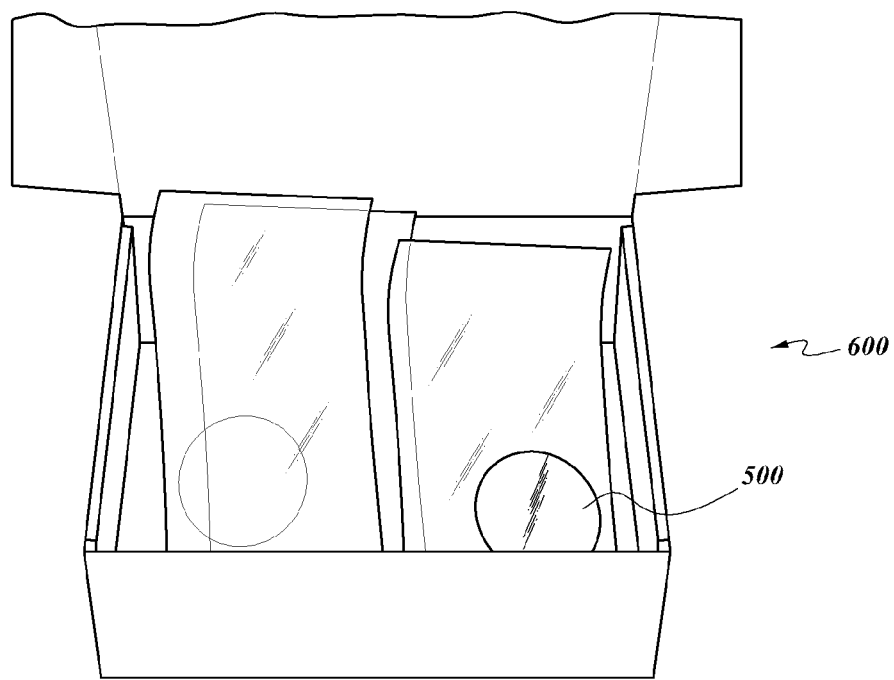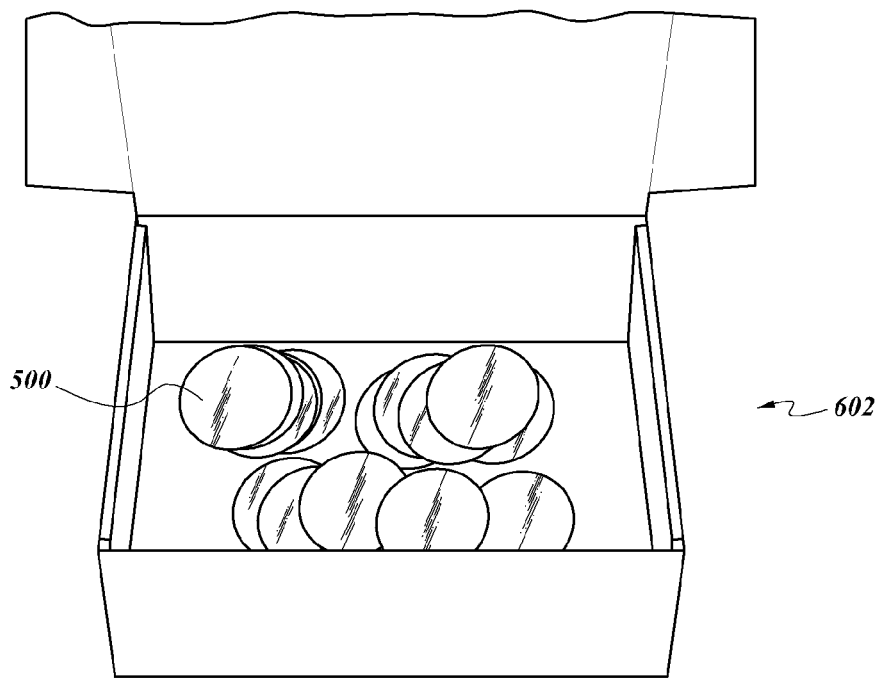
FIG. 9

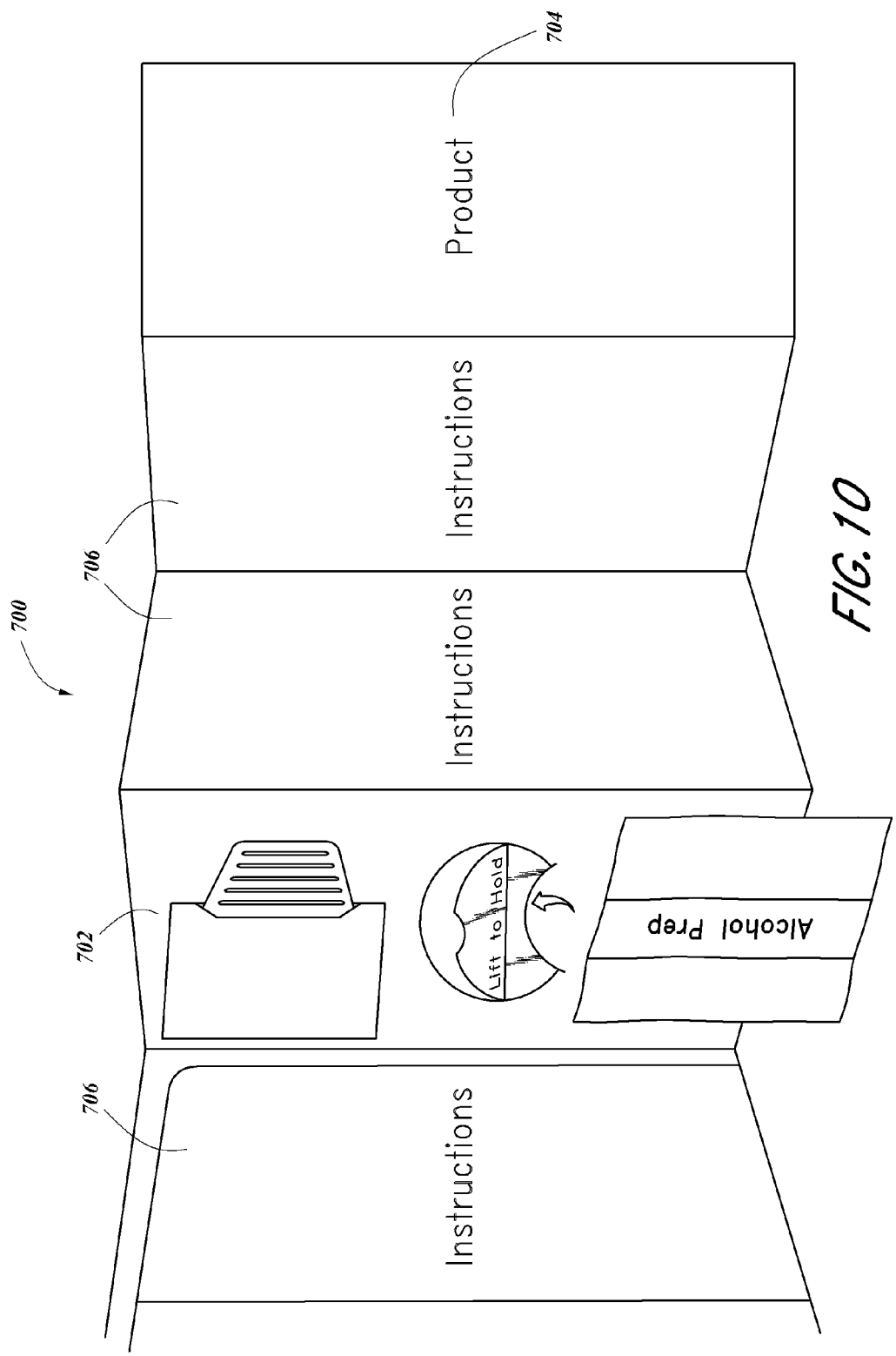

SKIN ABRADER

CROSS-REFERENCE TO RELATED APPLICATIONS

This application is a divisional of U.S. application Ser. No. 14/247,014, filed Apr. 7, 2014, entitled SKIN ABRADER, which claims the benefit of U.S. Provisional Application No. 61/809,817, filed Apr. 8, 2013, entitled SKIN ABRADER. The contents of the aforementioned applications are hereby incorporated by reference in their entirety as if fully set forth herein. The benefit of priority to the foregoing application is claimed under the appropriate legal basis, including, without limitation, under 35 U.S.C. §119(e).

BACKGROUND OF THE INVENTION

1. Field of the Invention

This application describes embodiments of apparatuses, methods, and systems for the abrasion of skin in preparation for application of an electrode for detection of cardiac and other low level electrical signals generated within the human body, allowing for improved short term and long-term adhesion and improved conductance through skin, resulting in better signal quality of recorded data.

2. Description of the Related Art

Skin contact electrodes are used extensively for detecting and transforming potentials generated within the body into electrical signals which may be monitored for a variety of functions, such as the preparation of electrocardiograms and electroencephalograms. Many disposable electrode assemblies and similar devices utilize an electrode together with an adhesive for holding the electrode in position on the skin. For the best electrical contact with mammalian skin, it is desirable to remove hair and a portion of the epidermis, as well as surface oils. Typically, the process involves removal of hair by shaving or other depilatory method. Next, the skin is abraded for the removal of the dry layers of stratum corneum, followed by cleaning and defatting of the skin using an alcohol wipe. The skin abrasion process exposes more conductive layers of skin to improve electric connection, promoting better transmission of a cleaner signal.

As mentioned previously, electrodes may contain an adhesive to keep the electrode in contact with the skin. The outer layers of the stratum corneum are typically the driest and nearest to being sloughed off by the body. Removing these cells prior to electrode placement allows the adhesive to come into newer, more anchored layers of the skin, promoting longer adhesion performance. With sensing applications that require longer-term wear periods, sufficient removal of skin takes on greater importance. The development of a long-term recording ECG patch has further created a need for a tool that is effective in thoroughly removing the stratum corneum layers, to allow for patch adhesion for periods up to and beyond 14 days.

As critical as the skin abrasion process is for good signal conduction and long term adhesion, it is a process that is often incomplete in practice. This is largely due to the limitations of existing abrasion tools in combination with the limited time and attention typically given to the abrasion process. Certain abrasion tools, resembling woven polymer sponges, have a coarse texture. Though the sensation of abrasion is heightened for the patient, the contours of the tool's surface are more conducive to creating scratches in the skin than evenly removing the outer stratum corneum layer. Other products, such as pumice-impregnated alcohol wipes, do an adequate job of abrading the skin without causing unwanted injury to the skin, however significant pressure and attention is required for an effective outcome. In combining the skin abrasion and cleaning step into a single tool, these instruments are easily confused for alcohol wipes intended for just cleaning, and the pressure required for abrasion is not achieved.

Because of the limitations of existing skin abrasion tools, there is need for a simple, one-piece, disposable and low-cost tool that can effectively abrade the skin while being easy to manipulate and that minimizes the amount of attention that must be given to this part of the prep process.

SUMMARY OF THE INVENTION

Embodiments of the present invention relate to skin abrasion devices. In one embodiment, a skin abrasion device comprises: a flat abrasive surface with a rounded shape and a holding layer to facilitate handling the device while applying even pressure to the skin. The device can be used in advance of skin-surface application of electrodes or devices that contain electrodes for sensing biopotentials such as an ECG. In some embodiments, the skin abrasion tool enables even and thorough removal of the top layer of stratum corneum without causing injury to the skin in the form of scratches or gouges, regardless of the experience level of the user.

In one embodiment, a dermal preparation device for preparation of the stratum corneum of a patient for long term adhesion of an electrode to the patient, comprises:
  a support layer having an upper surface, a lower surface, a major axis extending through a geometrical center of the support layer and along the longest dimension of the support layer;
  an abrasive adhered to the lower surface;
  a handle secured to the upper layer; and
  wherein the handle is formed by bonding a first portion of a handle layer to the support layer, and folding a second portion of the handle layer to form the handle.

In some embodiments, the support layer of the dermal preparation device is approximately circular, and the major axis is a diameter of the circle. In certain embodiments, the major axis is no more than about 2.5 inches long. In further embodiments, the is no more than about 2.0 inches long. Certain embodiments may cal for the dermal preparation device to further comprise an atraumatic edge. In some embodiments, the atraumatic peripheral edge comprises a rounded surface formed by inclining a peripheral edge of the device away from a plane defined by the lower surface, in the direction of the upper surface. In further embodiments, the support layer is sufficiently flexible that when pressed against a dermal surface using the handle, the lower surface will deform into a convex surface against the dermal surface. In some embodiments, the handle is bonded to the support layer along a bond which extends at least about 50% of the maximum dimension of the support, along the axis of the bond. In certain embodiments, the handle is bonded to the support layer along a bond which extends at least about 85% of the maximum dimension of the support, along the axis of the bond. In further embodiments, the handle is bonded directly to the support layer. In certain embodiments, the handle is bonded to the support layer by a bond which covers at least about 15% of the total area of the upper surface of the support layer. In certain embodiments, the handle is bonded to the support layer by a bond which covers at least about 35% of the total area of the upper surface of the support layer. In some embodiments, the abrasive comprises a grit ranging from about 36-66 µm.

In further embodiments, in a dermal preparation device as described above where the handle is bonded to the support layer along a bond which extends at least about 50% of the maximum dimension of the support along the axis of the bond, the axis of the bond is substantially parallel to the major axis. In some embodiments, a transdermal electrode and surface preparation kit, comprises at least one transdermal electrode configured for adhesive attachment to a patient's skin, and at least one dermal preparation device as described above.

In some embodiments, a dermal preparation device for preparation of the stratum corneum of a patient for long term adhesion of an electrode to the patient, comprises:
 an abrasive surface;
 an inner layer; and,
 a holding layer further comprising a gripping portion.

In certain embodiments, a method of abrading the skin of patient via a dermal preparation device in preparation for the long term adhesion of an electrode, comprises:
 placing the dermal preparation device on the skin;
 grasping a gripping portion of the dermal abrasion device;
 applying pressure to the skin through the dermal abrasion device; and
 moving the device in a manner to remove a desirable amount of skin.

In some embodiments, the method may comprise preparing the skin for application of the dermal preparation device. Certain embodiments may call for the method to further comprise adhering a physiological monitoring device that comprises an electrode. In embodiments of the method, a physiological parameter may be measured with the physiological monitoring device. In embodiments, the desirable amount of skin comprises an amount of skin configured to improve the signal quality of the physiological monitoring device.

BRIEF DESCRIPTION OF THE DRAWINGS

FIG. 5 illustrates a method for the manufacture of skin abrasion devices.

FIG. 6 illustrates an additional method for the manufacture of a skin abrasion device.

FIGS. 7A-B illustrate embodiments of packaging for a skin abrasion device.

FIG. 9 illustrates an embodiment of a kit containing skin abrasion devices.

FIG. 10 illustrates an embodiment of a kit containing materials related to prepping the surface of the skin for electrode placement.

DETAILED DESCRIPTION

Embodiments disclosed herein relate to apparatuses and methods directed towards the use and manufacture of skin abrasion devices.

Figure 1A:
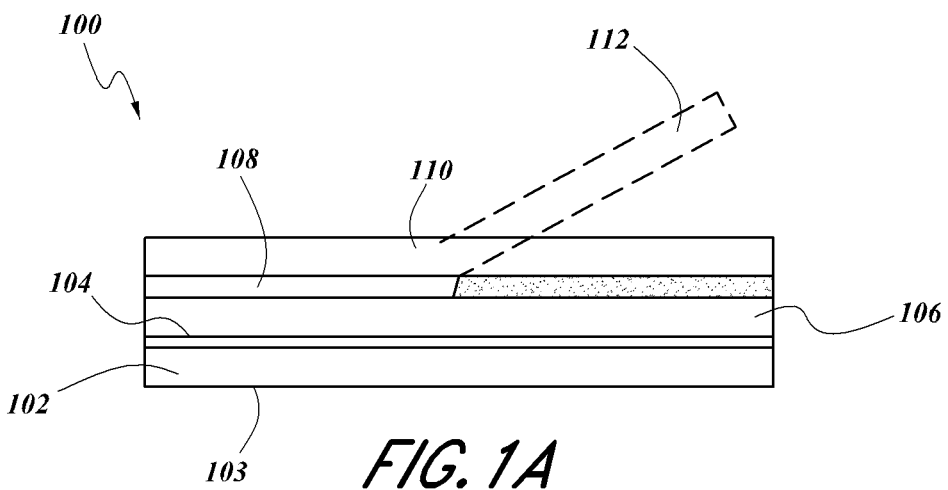
FIGS. 1A-B illustrate different views of embodiments of a skin abrasion device.

FIG. 1A illustrates an embodiment of a skin abrasion device 100 comprising an abrasive layer 102 with an abrasive surface 103, an adhesive layer 104, an inner sheet 106, a partial adhesive layer 108, and a holding layer 110 further comprising a gripping portion 112. The skin abrasion device 100 may be flexible and can be further configured to remove at least a portion of the stratum corneum. An advantage of ensuring properties of flexibility and resilience in the abrasion device is the ability to conform against the curvature and contours of the body where electrodes would be placed, while maintaining a relatively even plane such that the pressure applied to the skin during abrasion can be substantially uniformly distributed across the surface as best as practicable.

It will be understood by one skilled in the art that the geometric shapes of the peripheral edge of the skin abrasion device described herein are non-limiting. The embodiments of the skin abrasion device described herein are applicable to a wide variety of geometric shapes.

In some embodiments, the abrasive layer 102 can comprise a material sheet such as medical grade or equivalent sandpaper, where a range of grit sizes can be used depending upon the level of abrasion or gentleness desired as well as the type of skin that is being abraded. In some embodiments, the average diameter of the grit may range in size from about 16-93 microns (µm). For example, the grit can have an average diameter ranging from: about 20-90 µm, about 25-85 µm, about 30-80 µm, about 35-75 µm, about 40-70 µm, about 45-65 µm, or about 50-60 µm. Preferably, Grit diameters in the range of 36-66 µm can provide a level of abrasion that is effective with minimal pressure and a perception of minimal roughness by the subject being abraded.

In some embodiments, the abrasive surface 103 may be a surface that is embedded with or bonded to abrasive material, such as polymeric or mineral particles, or one that is textured through material properties or a manufacturing process.

Preferably, the abrasive surface 103 is biocompatible. In one embodiment, the abrasive surface 103 may comprise a biocompatible mineral such as silicon carbide. Another embodiment may be a biologically inert polymer that is formed or molded to have an abrasive texture, such as hook and loop fasteners. Further embodiments include the use of aluminum oxide, alumina-zirconia, chromium oxide, ceramic aluminum oxide or any other appropriately abrasive material.

In some embodiments, the abrasive surface 103 may comprise commercially available abrasive surfaces such as 426U Abrasive, available from 3M Innovative Properties Company. Further abrasive surfaces may also include those described in U.S. Pat. No. 6,136,008, SKIN ABRASION DEVICE FOR BIOMEDICAL ELECTRODE, filed Mar. 19, 1998 and hereby incorporated by reference. For example, as described in U.S. Pat. No. 6,136,008, an abrasive surface can comprise: a polymeric geometrically structured surface abrasive which minimizes and preferably avoids any use of mineral particle content, making the assembly of a skin abrasion device in a high-speed, low-cost biomedical electrode manufacturing facility possible under GMP/QSR conditions; and a predetermined pattern of geometrically structured surface abrasive, which permits assured, engineered surfaces for consistent abrading properties on a specific type of mammalian skin or a specific mammal, in order to achieve reduced skin impedance without undue damage or pain to the patient. Using these parameters, it is possible to engineer a geometrically structured surface abrasive based upon the tooling used to produce such surface.

As further described in U.S. Pat. No. 6,136,008, a portion of an abrasive surface can be engineered from a variety of polymeric materials. Non-limiting examples of such polymers include (meth)acrylates such as triacrylates prepared from one or more monomers such as trimethyolpropane triacrylate and triacrylate of trishydroxyethyl isocyanate. Additives can be added to such an abrasive surface and can include pigments, dyes, plasticizers, anti-oxidants, and fillers as desired by those skilled in the art.

The embodiments described herein may further include the use of open-coat abrasives or perforations, in order to minimize the collection of abraded skin that may reduce the effectiveness of the abrasive during the time of use.

In certain preferable embodiments, the material properties of the selected abrasive material sheet used in the abrasive layer 102 contribute to the flexibility and structural resilience of the abrasive device. In some embodiments, the abrasive surface 102 can be laminated to the inner sheet 106 via an adhesive layer 104. Adhesive layer 104 can comprise any suitable adhesive material, for example a double-sided rubber adhesive such as 300LSE manufactured by 3M Innovative Properties Company. In some embodiments, adhesive layer 104 is a glue or other adhesive material sheet or substance.

In certain embodiments, the inner sheet 106 can be a flexible sheet or film, preferably constructed from a polymer such as polythethylene terephthalate. In other embodiments, the inner sheet 106 can comprise any suitable polymer, for example polyethylenes, polypropylenes, polyesters, vinyl esters, other flexible polymer films. The thickness of the inner sheet 106 can range from about 0.002 inches to 0.015 inches. For example, the thickness of the inner sheet 106 can range from: about 0.003-0.014 inches, about 0.004-0.013 inches, about 0.005-0.012 inches, about 0.006-0.011 inches, about 0.007-0.010 inches, or about 0.008-0.009 inches. The use of a flexible polymer film advantageously contributes to the flexibility and structural resilience of the skin abrasion device.

In certain embodiments, the thickness of the inner sheet 106 is desirably selected to complement the material properties of the abrasive layer. For example, if the abrasive layer is particularly thick, then a thinner inner sheet layer may be more desirable.

Another advantage of laminating the inner sheet 106 to the abrasive surface 102 is the minimization of creases that can form on the abrasive surface, as certain abrasive materials can be prone to crease-forming due to bending. Such creasing can produce sharp corners which may scratch or break the skin, increasing the likelihood of skin irritation or sensitization to electrode materials.

In some embodiments, the inner sheet 106 is attached to an adhesive layer 108 that covers less than 100% of an upper surface of the inner sheet 106. The partial adhesive layer 108 can be comprised of any suitable adhesive material, for example a double-sided rubber adhesive such as 300LSE manufactured by 3M Innovative Properties Company. In other embodiments, the adhesive layer 108 is a type of glue or other adhesive substance. In some embodiments, the adhesive layer 108 can cover a portion of the inner sheet 106 ranging from approximately 5% to 100% of inner sheet 106. For example, the portion of inner sheet 106 covered by adhesive layer 108 can be at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, or about 100% of the total top area of the inner sheet 106. In certain embodiments, the adhesive layer 108 covers no more than about 60% or no more than about 50% of the area of the inner shet 106. In alternative embodiments, the inner sheet 106 can comprise multiple thinner sheets laminated together.

In some embodiments, the holding layer 110 can be attached to the inner sheet 106 via an adhesive layer 108. The adhesive layer 108 can be attached to only a portion of the holding layer 110. As will be described in greater detail below, the portion of the holding layer 110 that is not attached to the adhesive layer 108 functions as the gripping portion 112, which can be a tab, handle, or other protrusion. The gripping portion 112 can be grasped between the fingers of a user to control the movement and applied pressure of the skin abrasion device.

In some embodiments, the portion of the holding layer 110 attached to the adhesive layer 108 can be at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, or about 100% of the total area of the holding layer 110. In certain embodiments, the portion of the holding layer 110 that is attached to the inner sheet 106 by adhesive layer 108 is no more than about 70%, about 60%, or about 50% of the area of the holding layer 110.

In certain embodiments, the holding layer 110 can be a flexible sheet or film, preferably constructed from a polymer such as polythethylene terephthalate. In other embodiments, the holding layer 110 can comprise any suitable polymer, for example polyethylenes, polypropylenes, polyesters, vinyl esters, or other flexible polymer films. The thickness of the holding layer can range from about 0.001-0.010 inches. For example, the thickness of the holding layer 110 can range from: about 0.002-0.009 inches, about 0.003-0.008 inches, about 0.004-0.007 inches, or about 0.005-0.006 inches.

In some embodiments, the holding layer 110 can be printed to include text instructions, diagrams, images, or other labeling that facilitates use of the device for certain applications, or that aid in correct selection of the device as applicable to cases in which multiple abrasion devices are provided to the user. For example, a visual indicium such as a number symbol or color code may be provided on the holding layer, or visible through the holding layer, indicative of a particular coarseness of the abrasive layer 102. In certain embodiments, a plurality of abrasion devices may be provided, each having two unique abrasive characteristics and unique corresponding indicium.

In some embodiments, the abrasive layer is not comprised of a separate layer, but rather, the bottom layer of the abrasive device is comprised of grit as described above, directly adhered to the inner sheet 106 via an adhesive.

Figure 1B:
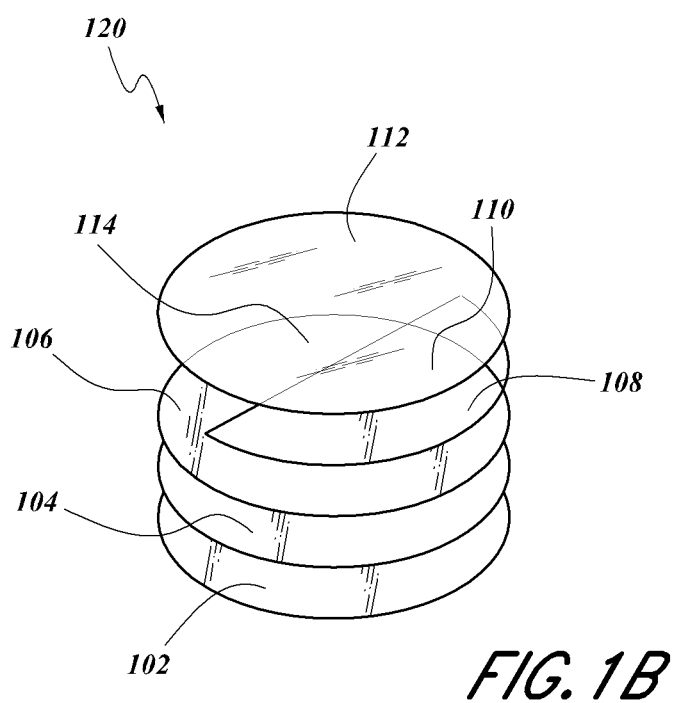
Figure 2A:
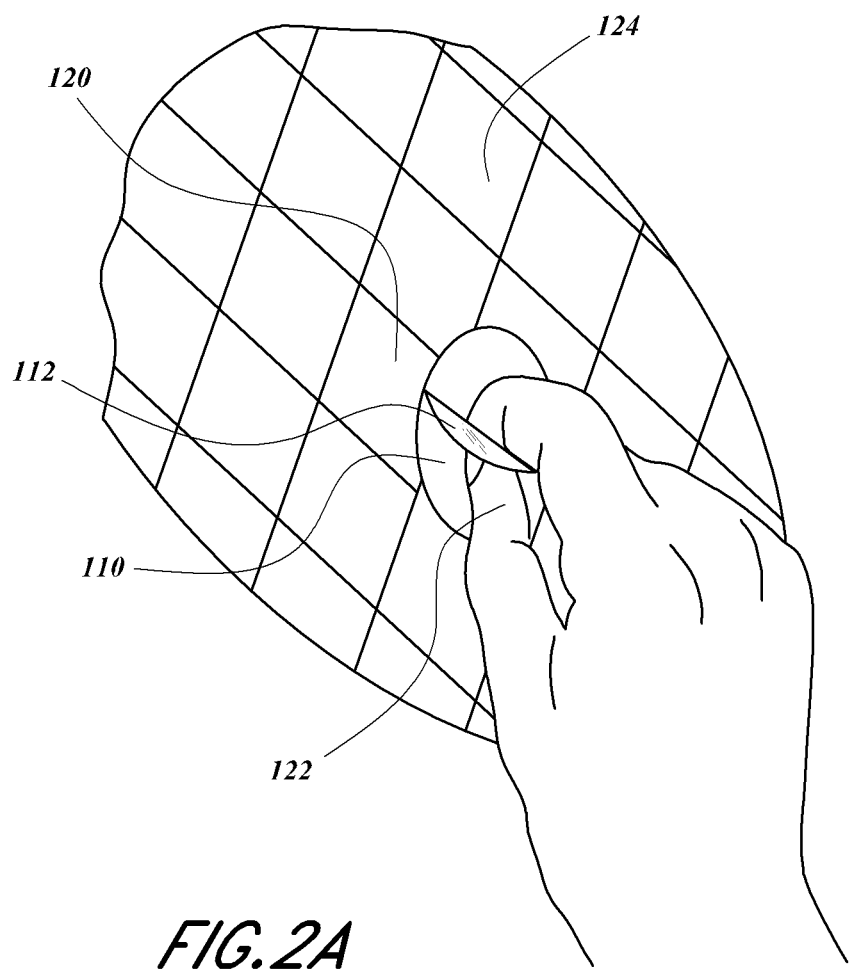
FIGS. 2A-E illustrate different views and photographs of embodiments of a skin abrasion device.
Figure 2B:
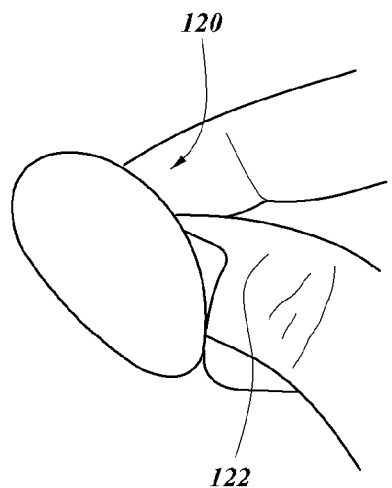
Figure 2C:
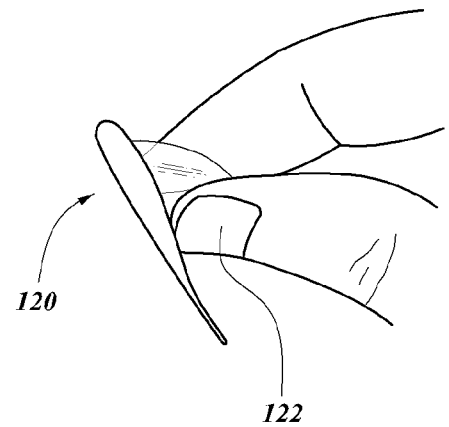
Figure 2D:
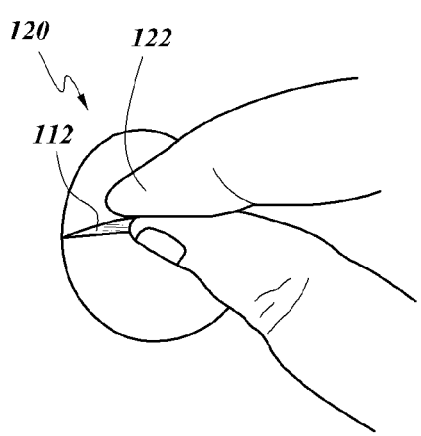
Figure 2E:
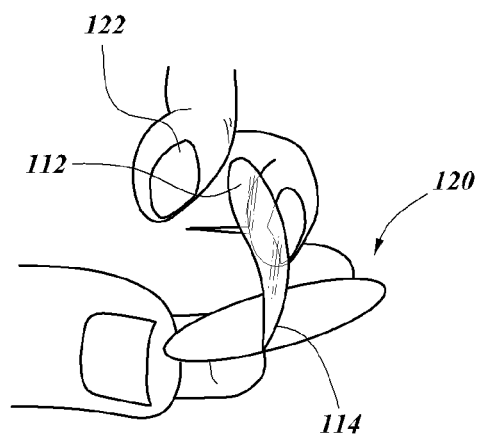

FIG. 1B illustrates an embodiment of a skin abrasion device with a circular peripheral shape 120. In some embodiments, the abrasive device 120 may be rounded, circular, oval, or otherwise curved. With a rounded shape, the abrasive device remains free of the types of angled or straight edges that can scratch, cut, or break the skin of the subject during the abrasion process when the device is moved back and forth with application of pressure. The abrasive device 120 may be made into further shapes without sharp or jagged edges unconfined to the aforementioned shapes. Similar to FIG. 1A, In some embodiments, the portion of the holding layer 110 attached to the adhesive layer 108 can be at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, or about 100% of the total area of the holding layer 110. In certain embodiments, the portion of the holding layer 110 that is attached to the inner sheet 106 by adhesive layer 108 is no more than about 70%, about 60%, or about 50% of the area of the holding layer 110.

In some embodiments, the abrasive device comprises a major axis 114 comprising the longest dimension that extends across the geometric center of the device in a plane parallel to the plane of the abrasive device. The length of the major axis 114 can range from about 0.5-3.0 inches. For example, the length of the major axis can range from: about 0.75-2.75 inches, about 1.0-2.5 inches, about 1.25-2.25 inches, or about 1.5-2.0 inches. In a preferred embodiment, the length of the major axis is 1.625 inches.

FIGS. 2A-F illustrate different views of an embodiment of an abrasive device, similar to the device described in FIG. 1B, wherein a holding feature such as the gripping portion 112 of the holding layer 110 can be pinched between the fingers 122 and used to abrade the skin 124. The gripping portion, which may be embodied as a tab, handle, or other protrusion, serves to facilitate secure holding of the abrasion device while minimizing contact between the abrasion device's user and the skin of the subject being abraded. The gripping portion also enables the clinician or wielder of the abrasion device to apply even pressure to the center of the abrasion device rather than uneven pressure to one edge, as may be the case if a flat piece of abrasive material were held without a holding feature. In a preferred embodiment, the gripping portion 112 of holding layer 110 extends across at least approximately half of the abrasive device as defined by the major axis 114. In some embodiments, the gripping portion 112 has the approximate shape of a half-circle. Preferably, the flat edge of the half-circle gripping portion 112 can extend across the entirety of major axis 114. However, in some embodiments, the flat edge of the gripping portion 112 extends along only a portion of the major axis 114. For example, the flat edge can extend across: at least about 10%, at least about 20%, at least about 30%, at least about 40%, at least about 50%, at least about 60%, at least about 70%, at least about 80%, at least about 90%, or about 100%. Further, it will be understood that the gripping portion 112 is not limited to a flat edge aligning with the major axis 114. In some embodiments, the flat edge of the gripping portion may be located parallel to the major axis between the major axis and the edge of the abrasive device. In other embodiments, the flat edge of the gripping portion may be perpendicular to the major axis 114. As will be understood by those skilled in the art, in still other embodiments, the shape of the gripping portion may be rectangular, circular, or further shapes other than a half-circle.

Figure 3:
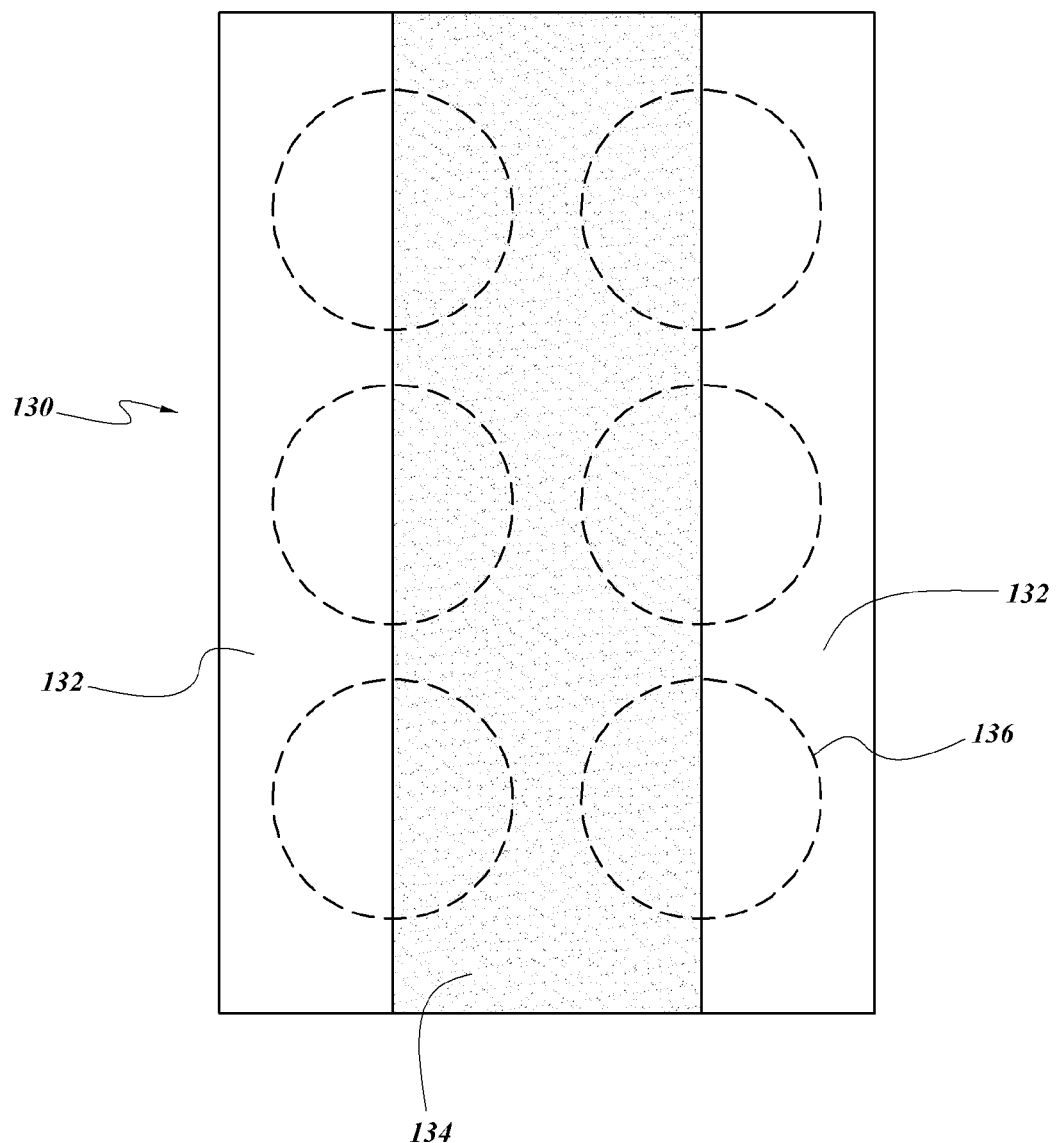
FIG. 3 illustrates an embodiment of a sheet for use in manufacturing a skin abrasion device.

FIG. 3 illustrates a sheet 130 for use in one method of manufacturing the abrasion device as described above, comprising disc cut-outs 136, partial adhesion layer 134, and unadhered sections of holding layer 132. In some embodiments, a method of producing the skin abrasion device comprises: laminating the aforementioned abrasive surface with a backing material, or multiple materials, for structural support and flexibility; attaching material that is used as a holding feature; and, cutting the material to a desired shape.

Within the aspect of manufacturing, the use of an abrasive film or sheet 130 facilitates the use of scalable and inexpensive converting methods for laminating to other necessary materials. In one embodiment of this process, as illustrated in FIG. 3, two abrasive discs 136 can be made as mirror images within the same 2-up die strike. This approach could be repeated in a pattern in both x and y dimensions, utilizing either a flat steel-rule die or a rotary die for large-scale production.

In some embodiments, the abrasion device comprises a topmost support layer and a handle. In certain embodiments, the handle can be attached to the support layer via two or more attachment points. Preferably, the two or more attachment points can be spaced apart for further stability. In some embodiments, the attachment points for the handle can be located in any location across the top surface of the abrasion device.

Figure 4:
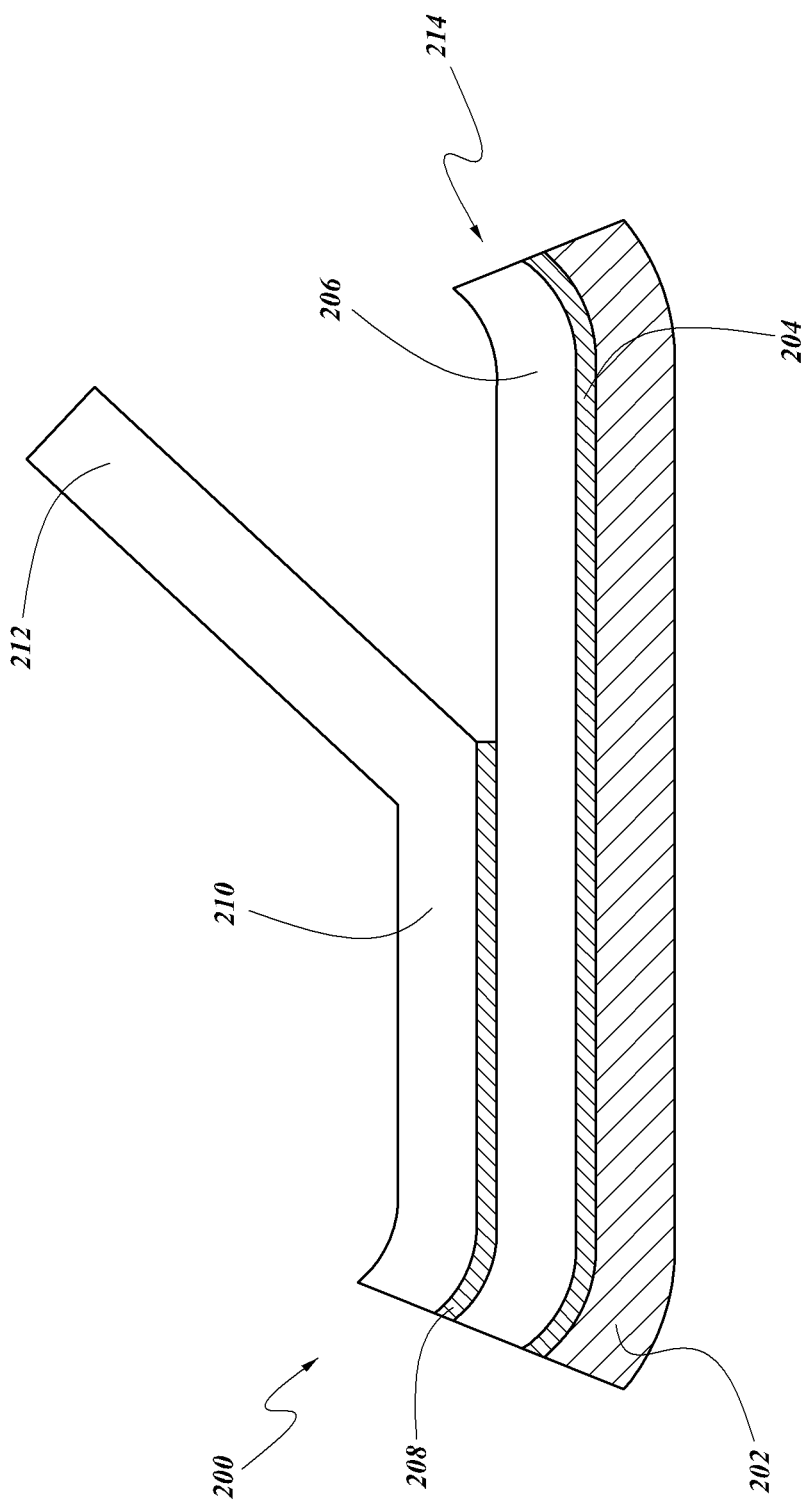
FIG. 4 illustrates an additional embodiment of a skin abrasion device.

FIG. 4 illustrates an embodiment of an abrasive device similar to the embodiments described in FIGS. 1-2 that is formed to have a slight upwardly concave shape, particularly at the edges, forming an atraumatic periphery 214. The abrasion device can have a rounded profile in plan view. In further embodiments, the abrasion device may have a rectangular, oval, or other shape in plan view. As with FIGS. 1-2, the abrasive device can comprise an abrasive layer 202, an adhesive layer 204, an inner sheet 206, a partial adhesive layer 208, and a holding layer 210 comprising a gripping portion 212. The atraumatic periphery 214 concaves upwardly and presents a convex curve along the peripheral lower edge which would reduce the risk of contact between skin and the potentially sharp edges of the abrasive device, further eliminating potential for inadvertent scratching or gouges in the skin. In some embodiments, the annular atraumatic surface can be formed by molding or thermoforming operations or by cold stamping the device or support layer from a sheet stack. An atraumatic periphery can alternatively be formed by tapering the thickness of the abrasion device towards the edges or by using lower stiffness materials to construct an annular peripheral zone on the device.

As similarly described above in relation to FIG. 1, the thickness of inner layer 206 can be varied, generally between about 0.001-0.015. A thicker inner layer 206 beyond about 0.01 may lead to decreased flexibility in the abrasive device; however, depending upon the construction material, a thicker inner layer can allow for greater ease in curving the edges of the device.

FIG. 5 illustrates an embodiment of a method 300 for creating the concave shape of the abrasive device of FIG. 4 through a cutting method using cutters 306 applied against a softer surface 304, causing the abrasive device 302 to take a curved edge 308. FIG. 6 illustrates an embodiment where preparation of the concave shape can be achieved through more deliberate forming methods 400 after the material is cut. In some embodiments, the material could be cut against an explicitly concave surface 404, imparting that shape when the cut force is applied.

Figure 7B:
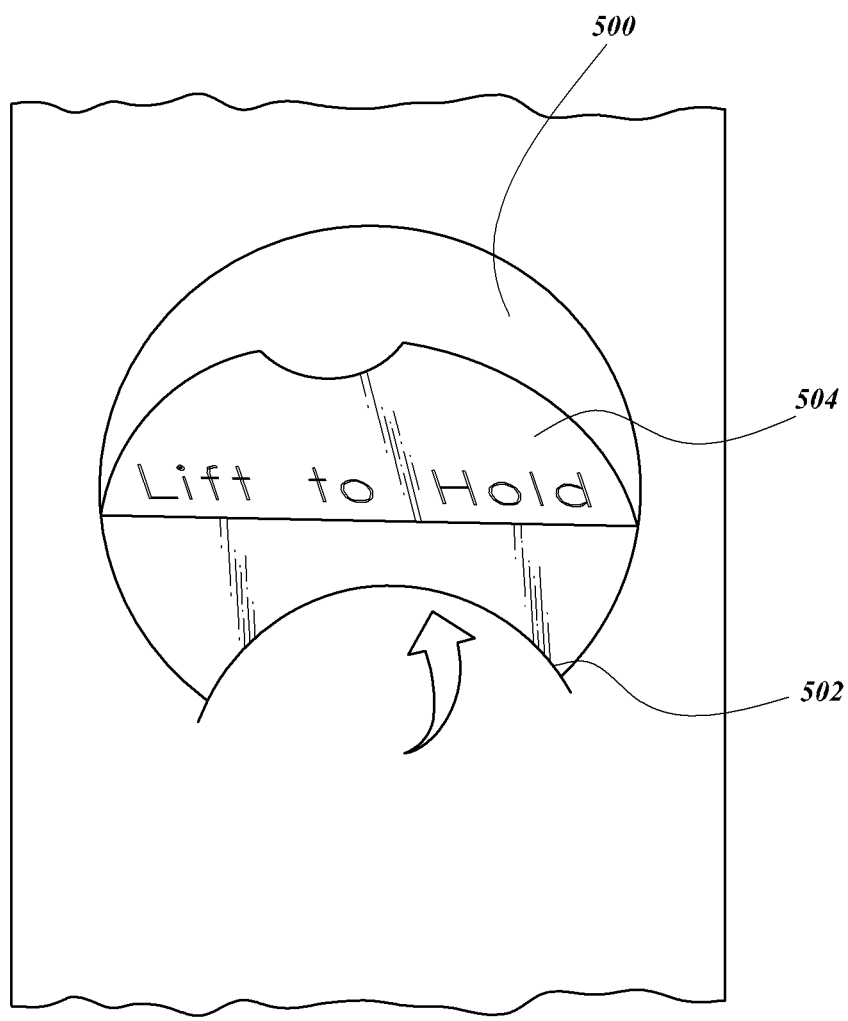

The shape and form of the abrasion device is conducive to flat and user-friendly packaging. FIG. 7A illustrates an embodiment of a mechanism for packaging the abrasion device 500 via a half-moon slit 502, where the tab or handle 504 of the abrasion device is presented on top of the slit 502. FIG. 7B illustrates an embodiment of a mechanism for packaging the abrasion device 500 where the tab or handle 504 may extend in a direction away from the half-moon slit 502. In some embodiments, the tab or handle 504 may extend in an opposite direction, directly away from the half-moon slit 502. In certain embodiments, the tab or handle can extend in a direction perpendicular to the half-moon slit 502. It will be understood by one of skill in the art that the slit may be of any shape suitable for holding the abrasion device, for example an angular slit. The abrasion device may also be held by more than one slit, such as two slits, three slits, or more than three slits. The half-moon slit may be a slit extending through an arc of at least about 120° and preferably at least about 160°, or 180°, and may have a substantially constant radius or a curve conforming to a portion of an oval or ellipse.

Figure 8:
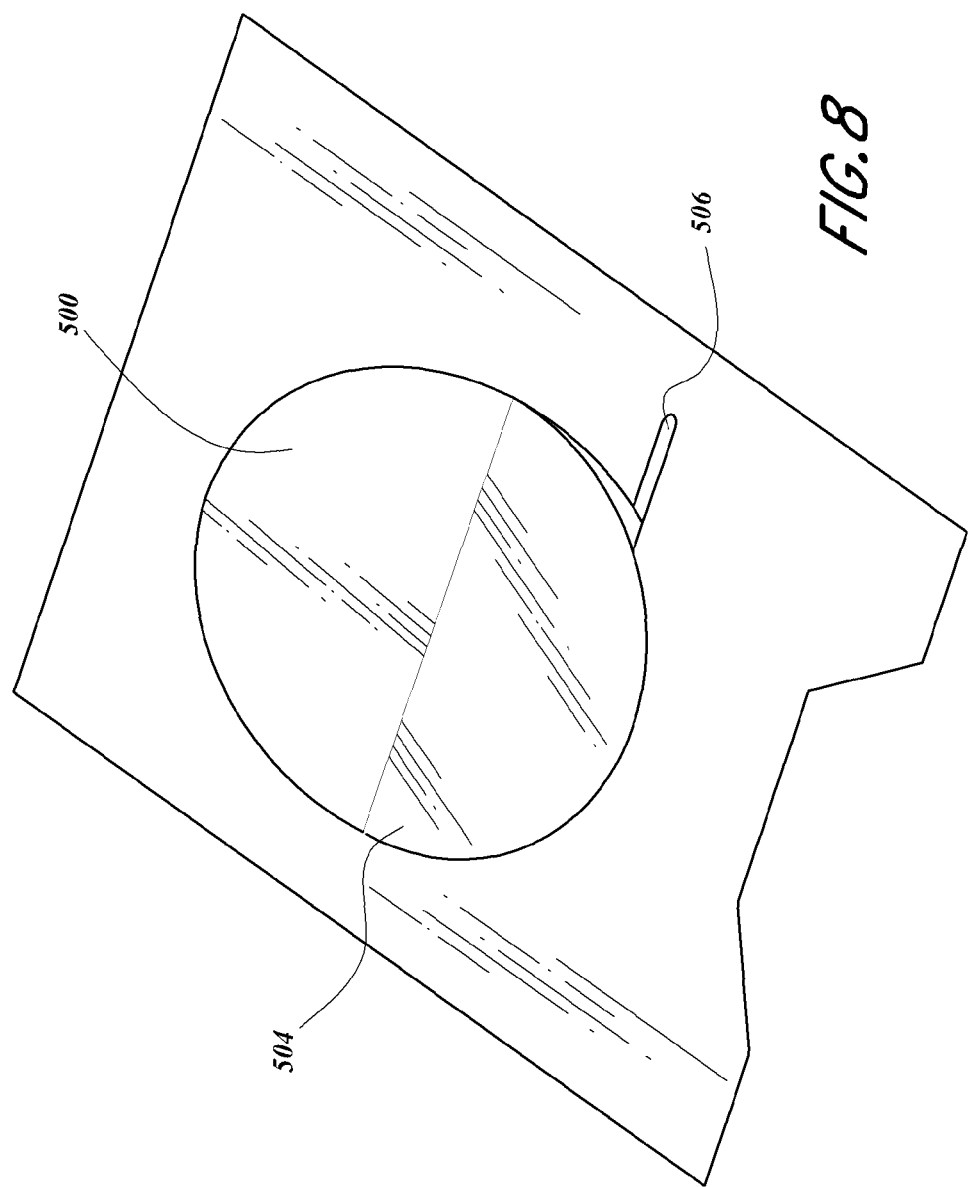
FIG. 8 illustrates an additional embodiment of packaging for a skin abrasion device.

FIG. 8 illustrates another packaging embodiment where the abrasion device is placed in a rectangular slot 506, which can secure the abrasion device through friction against the packaging surface, and presents a handle above or below the slot. Both of these embodiments described in FIGS. 7 and 8 allow the user to grip the abrasion device from the included tab or handle 504 and remove the device from the packaging without changing grip.

As described above, the abrasion device allows for versatility in its packaging. In one packaging embodiment, the abrasion device may be individually packaged and provided in multiple unit packaging 600. Alternately, many abrasion devices may be provided loose, in a box of multiple quantities 602. FIG. 9 illustrates a kit embodiment, in which a single, or multiple abrasion devices are provided for use with a single electrode or other physiological monitoring product.

In a kitted embodiment 700, the abrasion device's flat form factor allows for packaging within instructions along with other skin preparation materials, such as razors and alcohol wipes. FIG. 10 illustrates one embodiment of such a kit, a Zio Patch kitted assembly 704, which contains the monitor, shaving tool, abrading tool, and cleaning wipe(s) 702 packaged together within the application instructions booklet. Instructions 706 In another embodiment of the abrasion device included within a kit, multiple abrasion devices of varying coarseness could be provided for sequential steps of abrasion, such as a coarse abrasion device for the first pass, and a finer grit abrasion device for the final pass. In another embodiment of the abrasion device included within a kit in which multiple abrasion devices of varying coarseness could be provided for sequential steps of abrasion, the different abrasion devices could vary in size and shape so as to be distinguishable within the kit.

In certain embodiments, the handle contains cut-outs (semi-circular, triangular, rectangular, or any suitable shape) along its edge, giving the user a feature that helps peel the handle up from the main body of the device if it has not been folded up.

In some embodiments, the kit 700 may further include instructions for the use of the abrasion device in combination with a monitoring device. For example, the kit may include instructions 706 such as how to enroll in an online website related to the abrasion device. Further instructions may include advising a user as to properly planning for the placement of the physiological monitoring device, including shaving, abrading the skin, cleaning the skin, removal of the device, and proper application of the physiological monitoring device.

What is claimed is:

1. A method of abrading the skin of a mammal via a dermal preparation device in preparation for adhesion of an electrode, comprising:
    placing a dermal preparation device on the skin, the dermal preparation device comprising a support layer having an upper surface, a lower surface coated with an abrasive, and a major axis extending through a geometrical center of the support layer and along the longest dimension of the support layer;
    wherein the dermal preparation device comprises a gripping layer secured to the upper surface of the support layer, the gripping layer comprising an adhered portion adhered to the support layer, a gripping portion, and a fold between the adhered portion and the gripping portion;
    grasping the gripping portion of the dermal preparation device;
    applying pressure to the skin through the dermal preparation device;
    moving the dermal preparation device in a manner to remove a desirable amount of skin; and
    placing a physiological measurement device on the skin, the physiological measurement device configured for adhesive attachment to a mammal.

2. The method of claim 1, wherein the physiological measurement device is an electrode.

3. The method of claim 2, wherein the electrode is configured to measure a physiological parameter.

4. The method of claim 3, wherein the physiological parameter is cardiac rhythm data.

5. The method of claim 1, further comprising preparing the skin for application of the dermal preparation device.

6. The method of claim 1, wherein the abrasive comprises a polymeric grit with diameters ranging from about 36-66 the abrasive configured to mechanically remove a portion of the stratum corneum of the mammal.

7. The method of claim 6, wherein the abrasive uniformly coats the entirety of the lower surface.

8. The method of claim 1, wherein the dermal preparation device further comprises an outer peripheral edge, the outer peripheral edge curving along the entirety of a circle and having no corners.

9. The method of claim 1, further comprising measuring a physiological parameter with the physiological monitoring device.

10. The method of claim 1, wherein a desirable amount of skin comprises an amount of skin configured to improve the signal quality of the physiological monitoring device.

11. The method of claim 1, wherein the support layer is approximately circular and the major axis is a diameter of the circle.

12. The method of claim 11, wherein the major axis is no more than about 2.5 inches long.

13. The method of claim 11, wherein the major axis is no more than about 2.0 inches long.

14. The method of claim 1, wherein the support layer is sufficiently flexible that when pressed against a dermal surface using the gripping portion, the lower surface will deform into a convex surface against the dermal surface.

15. The method of claim 1, wherein the gripping portion is a handle.

16. The method of claim 15, wherein the handle is bonded to the support layer along a bond which extends at least about 50% of a maximum dimension of the support layer, along an axis of the bond.

17. The method of claim 16, wherein the axis of the bond is substantially parallel to the major axis.

18. The method of claim 15, wherein the handle is bonded to the support layer along a bond which extends at least about 85% of a maximum dimension of the support layer, along an axis of the bond.

19. The method of claim 15, wherein the handle gripping layer is bonded to the support layer by a bond which covers at least about 15% of a total area of the upper surface of the support layer.

20. The method of claim 15, wherein the handle gripping layer is bonded to the support layer by a bond which covers at least about 35% of a total area of the upper surface of the support layer.

21. The method of claim 1, wherein the dermal preparation device is separate from the physiological measurement device.

22. The method of claim 1, wherein the gripping portion extends above the upper surface of the support layer.

* * * * *

UNITED STATES PATENT AND TRADEMARK OFFICE
CERTIFICATE OF CORRECTION

PATENT NO. : 9,451,975 B2
APPLICATION NO. : 14/831078
DATED : September 27, 2016
INVENTOR(S) : Genaro Sebastian Sepulveda It is certified that error appears in the above-identified patent and that said Letters Patent is hereby corrected as shown below:

On the Title Page

Item (71), Applicant at Line 1, Change "iRhythmTechnologies," to --iRhythm Technologies,--.

In Column 1 (page 5, item (56)) at Line 4, Under Other Publications, change "holer" to --holter--.

In Column 1 (page 5, item (56)) at Line 11, Under Other Publications, change "caapana." to --capana.--.

In Column 2 (page 5, item (56)) at Line 1, Under Other Publications, change "24-hou" to --24-hour--.

In the Specification

In Column 2 at Line 45, change "the is no" to --the major axis is no--.

In Column 2 at Line 46, Change "cal" to --call--.

In Column 5 at Line 8, Change "trimethyolpropane" to --trimethylolpropane--.

In Column 5 at Line 30, Change "polythethylene" to --polyethylene--.

In Column 6 at Line 7, Change "shet" to --sheet--.

In Column 6 at Line 34, Change "polythethylene" to --polyethylene--.

In Column 9 at Line 36, Change "In" to --in--.

Signed and Sealed this
Twentieth Day of June, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,451,975 B2

In the Claims

In Column 10 at Line 30 (approx.), In Claim 6, change "36-66" to --36-66 µm,--.

In Column 11 at Line 1, In Claim 19, after "the" delete "handle".

In Column 11 at Line 5, In Claim 20, after "the" delete "handle".